United States Patent
Trieu et al.

(10) Patent No.: US 7,458,988 B2
(45) Date of Patent: Dec. 2, 2008

(54) COMPRESSIBLE CORPECTOMY DEVICE

(75) Inventors: Hai H. Trieu, Cordova, TN (US); Michael C. Sherman, Memphis, TN (US); Bret M. Berry, Jacksonville, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 635 days.

(21) Appl. No.: 10/701,547

(22) Filed: Nov. 5, 2003

(65) Prior Publication Data

US 2005/0096744 A1    May 5, 2005

(51) Int. Cl.
*A61F 2/44* (2006.01)

(52) U.S. Cl. .................................................. 623/17.13

(58) Field of Classification Search .... 623/17.11–17.16
See application file for complete search history.

(56) References Cited

U.S. PATENT DOCUMENTS

| | | | |
|---|---|---|---|
| 4,309,777 A | | 1/1982 | Patil |
| 4,759,769 A | * | 7/1988 | Hedman et al. .......... 623/17.13 |
| 4,932,969 A | | 6/1990 | Frey et al. |
| 5,236,460 A | | 8/1993 | Barber |
| 5,370,697 A | | 12/1994 | Baumgartner |
| 5,720,474 A | * | 2/1998 | Sugiyama ................ 267/249 |
| 5,776,198 A | * | 7/1998 | Rabbe et al. ............. 623/17.15 |
| 5,893,889 A | * | 4/1999 | Harrington .............. 623/17.16 |
| 6,015,436 A | * | 1/2000 | Schonhoffer ............ 623/17.16 |
| 6,045,579 A | | 4/2000 | Hochshuler et al. |
| 6,176,881 B1 | | 1/2001 | Schar et al. |
| 6,296,665 B1 | | 10/2001 | Strnad et al. |
| 6,352,556 B1 | | 3/2002 | Kretschmer et al. |
| 6,454,805 B1 | | 9/2002 | Baccelli et al. |
| 6,454,806 B1 | | 9/2002 | Cohen et al. |
| 6,468,310 B1 | | 10/2002 | Ralph et al. |
| 6,524,341 B2 | | 2/2003 | Lang et al. |
| 6,527,806 B2 | | 3/2003 | Ralph et al. |
| 2002/0082695 A1 | | 6/2002 | Neumann |
| 2002/0128716 A1 | | 9/2002 | Cohen et al. |
| 2003/0009223 A1 | | 1/2003 | Fehling et al. |
| 2003/0045877 A1 | | 3/2003 | Yeh |

FOREIGN PATENT DOCUMENTS

| | | |
|---|---|---|
| DE | 20019520 U1 | 2/2001 |
| EP | 0277282 | 8/1988 |
| EP | 0 950 389 | 10/1999 |

OTHER PUBLICATIONS

Patent Cooperation Treaty—European Patent Office, "Notification of Transmittal of The International Search Report and The Written Opinion of the International Searching Authority, or the Declaration," Jun. 2, 2005, 18 pages.

* cited by examiner

*Primary Examiner*—Bruce E. Snow
(74) *Attorney, Agent, or Firm*—Haynes and Boone, LLP

(57) ABSTRACT

A vertebral implant device for interposition between two vertebral endplates comprises an outer body and an inner body. The outer body movably engages the inner body. A core member positioned between the outer body and the inner body is at least partially compressed when a load is applied to the implant device.

23 Claims, 3 Drawing Sheets

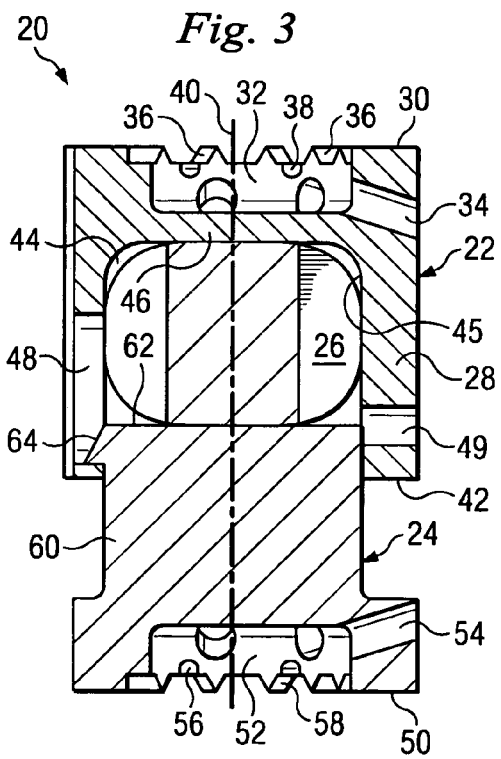
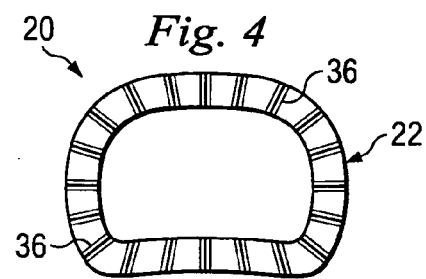
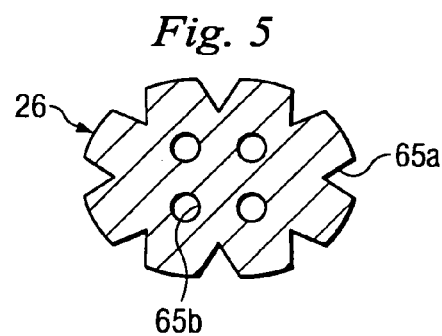
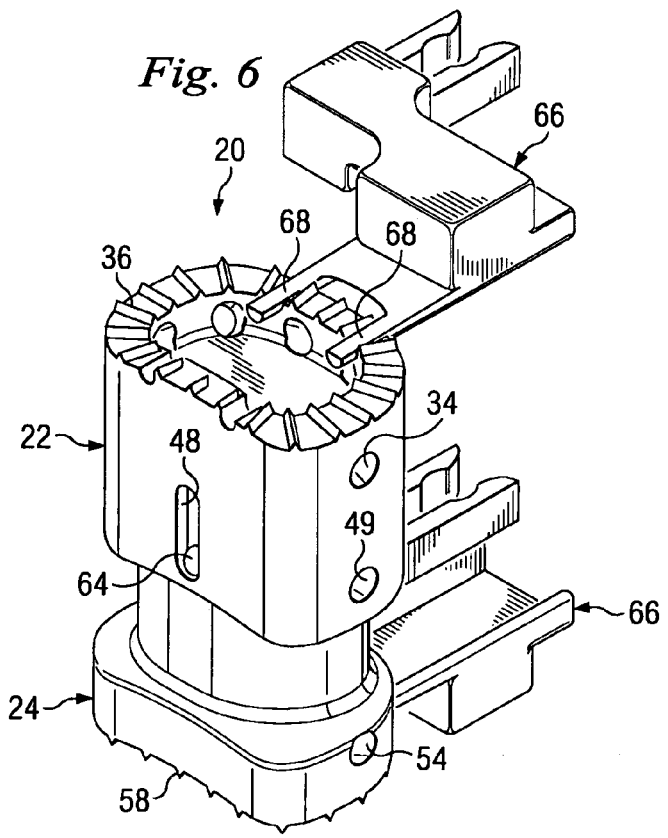

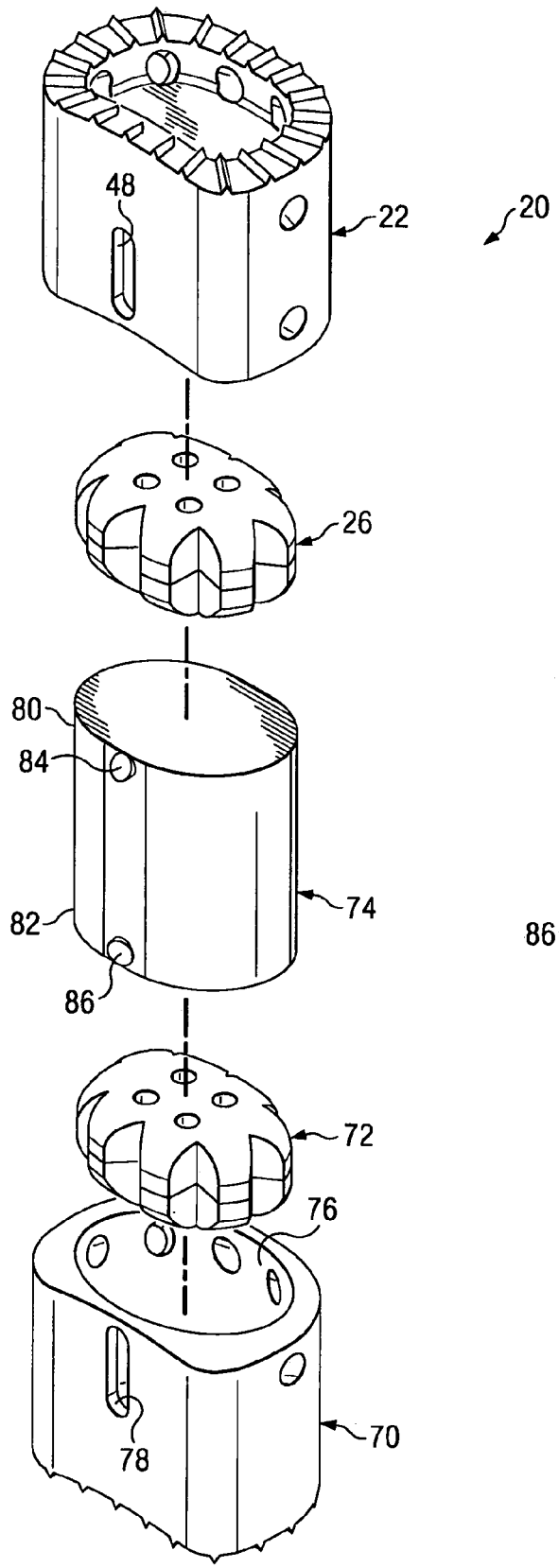
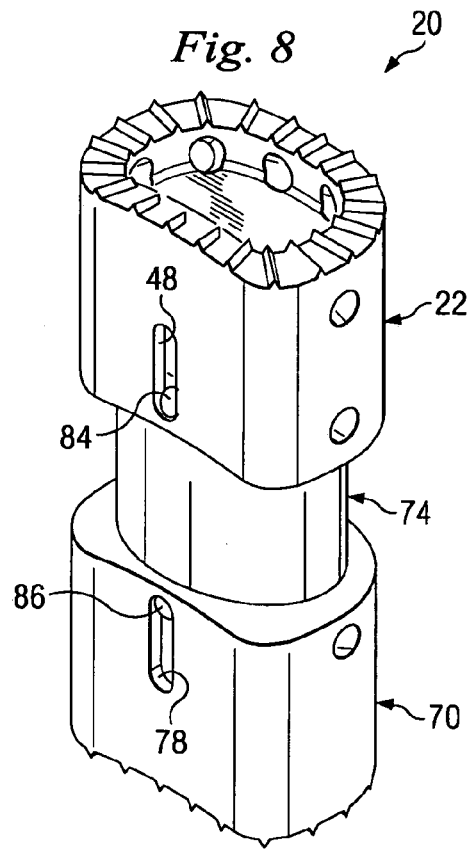

COMPRESSIBLE CORPECTOMY DEVICE

FIELD OF THE INVENTION

The present invention relates generally to an implant for replacement of one or more vertebral bodies and their adjacent discs, and more particularly, to a vertebral implant assembly having a compressible core component.

BACKGROUND

A variety of spinal injuries and deformities can occur due to trauma, disease, or congenital effects. These injuries and diseases can, ultimately, result in the destruction of one or more vertebral bodies and lead to a vertebrectomy or corpectomy in which the one or more damaged vertebral bodies and their adjacent discs are excised. Reconstruction of the spine following the vertebrectomy can present a number of challenges for the surgeon.

One surgical concern is securely interposing a vertebral implant between the remaining rostral and caudal vertebral bodies to allow the implant to resist dynamic loads, including axial, torsional, and shear loading, without undue subsidence or damage to the adjacent vertebral endplates. Therefore, a vertebral implant assembly is needed that can be installed with minimal injury to surrounding structures and that comprises durable components for dampening the affect of dynamic loading on the spine.

SUMMARY

This invention relates to a vertebral implant device for interposition between two vertebral endplates. The device comprises an outer body, an inner body, and a core member positioned between the outer body and the inner body. The outer body may be movably engaged with the inner body. Responsive to a load applied to the device, the outer and inner body may at least partially compress the core member.

In another embodiment, a vertebral implant device configured for interposition between two vertebral endplates comprises first and second outer bodies, a center shaft, and first and second core members. The first core member is positioned between the first outer body and the center shaft, and the second core member is positioned between the second outer body and the center shaft. The outer bodies may be movably engaged with the center shaft. Responsive to a load applied to the device, the outer bodies and the center shaft may at least partially compress the core members.

In still another embodiment, a vertebral implant device is installed between two vertebral endplates in a vertebral column using a method of the present invention. A core member may be positioned within an outer body of the device. The outer device may be placed in movable engagement with the inner body of the device with the core member positioned between the inner body and the outer body. An insertion instrument may be used to compress the device and position the device in the vertebral column.

BRIEF DESCRIPTION OF THE DRAWINGS

FIG. 2b is a perspective view of the assembled implant assembly of FIG. 2a.

FIG. 3 is a cross sectional view of the implant assembly of FIG. 2a.

FIG. 4 is a top view of the implant assembly of FIG. 2a.

FIG. 5 is a cross sectional view of the core member of FIG. 2a.

FIG. 6 is a perspective view of a vertebral implant assembly with an installation device.

FIG. 7 is an exploded perspective view of a vertebral implant assembly according to a second embodiment of the present invention.

FIG. 8 is a perspective view of the assembled implant assembly of FIG. 6.

DETAILED DESCRIPTION

Figure 1:
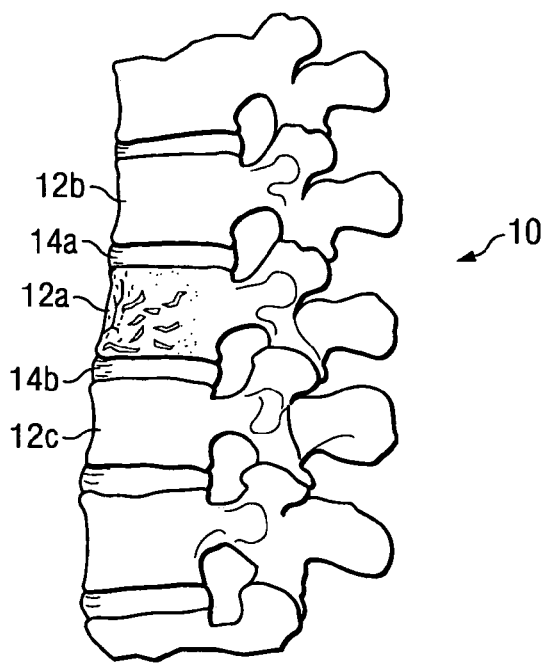
FIG. 1 is a side view of a destroyed vertebral body within a vertebral column.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral column with a damaged vertebra 12a extending between two intact vertebrae 12b and 12c. An intervertebral disc 14a extends between vertebral bodies 12a and 12b, and an intervertebral disc 14b extends between vertebral bodies 12a and 12c. In a typical surgical excision, the vertebra 12a is removed together with discs 14a and 14b creating a void between the two intact vertebra 12b and 12c. This procedure may be performed using an anterior, anterolateral, or other approach known to one skilled in the art. A vertebral implant assembly according to an embodiment of the present invention is then provided to fill the void between the two intact vertebrae 12b and 12c. Although the embodiment to be described is premised upon the removal of a single vertebra, it is understood that a different embodiment of the present invention may be inserted in an intervertebral disc space without the removal of a vertebrae when required by the surgical procedure. In still another embodiment, the present invention may be used in a vertebral column reconstruction following a vertebrectomy removing two or more diseased or damaged vertebrae and their adjacent discs.

Figure 2A:
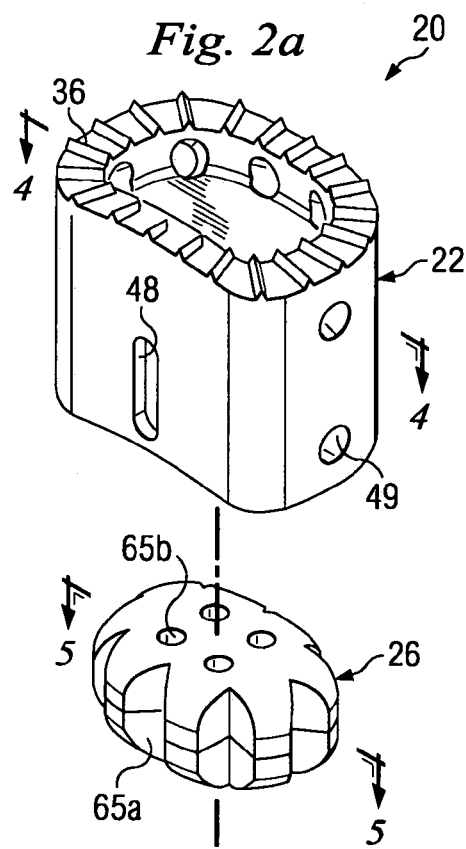
FIG. 2a is an exploded perspective view of a vertebral implant assembly according to one embodiment of the present invention.
Figure 2B:
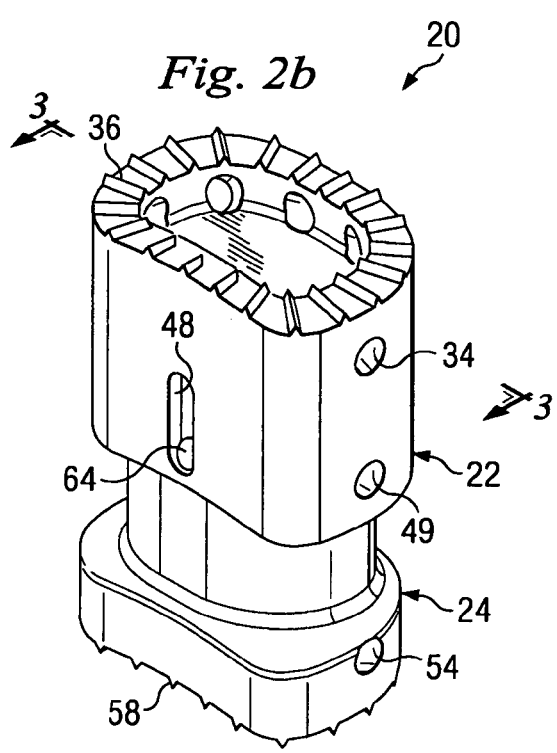

Referring now to FIG. 2a, a vertebral implant device according to an embodiment of the present invention is referred to, in general, by the reference numeral 20 and includes an outer body 22 and an inner body 24 between which a core member 26 may be positioned. FIG. 2b illustrates the components of FIG. 2a in an assembled condition in preparation for implantation in a vertebral column as will be described in detail below.

Referring now to FIG. 3, the outer body 22, includes a lateral wall 28 and an endwall 30. In one embodiment, endwall 30 includes a cavity 32 configured to accept bone growth promoting substances such as, but without limitation, bone graft material, bone morphogenetic protein (BMP), or other osteoinductive or osteoconductive material (not shown). To promote a secure and stabile interface between the implanted device 20 and the adjacent vertebrae in the vertebral column, one or more apertures 34 may preferably extend from the cavity 32 through the lateral wall 28, permitting bone growth in and around the outer body. The apertures 34 may further permit the movement of fluid into and out of the cavity 32. Although the apertures 34, as depicted in FIG. 3, may be directed away from the endwall 30, it is understood that they may be directed in any of a variety of orientations based upon the surgical application, the material used, or other design factors.

A plurality of protrusions 36 or other surface roughening may be formed on the endwall 30 to restrict movement of the implanted device 20. In some embodiments, the protrusions 36 may be relatively low ridges or textured areas on the endwall 30 which are adapted to engage the endplate of the adjacent vertebral body to maintain the position of the implanted assembly. In other embodiments, the protrustions 36 may be longer, cleat-like structures, which can penetrate the endplate of the adjacent vertebra to hold the implanted assembly in place. The endwall 30 may also or alternatively comprise one or more grooves 38 configured to accept the prongs of a compression and/or insertion instrument.

As shown in FIG. 3, the endwall 30 may be perpendicular to a longitudinal axis 40 of the of the outer body 22. However, in an alternative embodiment, the endwall 30 may form any of a variety of angles relative to the longitudinal axis 40 to accommodate a particular patient anatomy or to achieve a desired alignment. It will be appreciated that in certain regions of the spine, the vertebral endplates are disposed in a non-parallel relationship to establish kyphosis or lordosis. Although the outer body 22 may be generally cylindrical, as shown in FIG. 4, it can include curved or flat areas which allow the outer body 22 to more closely match the profile of the adjacent vertebra after surgical implantation. The outer body 22 may be formed in a variety of heights and widths and with a variety of endwall angulations. For example, the outer body 22 may have a height of approximately 32 mm. and an endwall angulation of 2°. A cross section of the outer body 22 perpendicular to the longitudinal axis 40 may have any of a variety of geometries and in certain embodiments may correspond to a cross section of the core member 26.

The outer body 22 may comprise an endwall 42 opposite the endwall 30. Through this endwall 42 a chamber 44, having chamber walls 45 and a chamber base 46, may be formed for housing the core member 26 and at least a portion of the inner body 24. In certain embodiments, the chamber 44 has smooth chamber walls 45 which curve into the chamber base 46. The smooth walls 45 can minimize abrasion which can damage the core member 26. The chamber 44 may conform closely to the shape of the core member or alternatively, may be shaped to comprise depressions, recessed areas, or other geometries into which the core member 26 may deform when subjected to loading.

An elongated slot 48 (see also FIGS. 2a and 2b) may extend longitudinally along the wall 28 of the outer body 22. The elongated slot 48 may extend through the wall 28 and in communication with the chamber 44. In an alternative embodiment, the slot 48 may extend only partially through the wall 28 without penetrating the exterior of the outer body 22. As will be described below, the slot 48 may be a retaining member used to connect the outer body 22 to the inner body 24. In an alternative embodiment, the outer body 22 may have a plurality of slots 48.

An aperture 49 may also extend through the wall 28 of the outer body 22 in communication with the chamber 44. In certain embodiments, a plurality of apertures 49 may extend through the wall 28. The aperture 49 may permit the evacuation of fluids or other material which may seize or otherwise restrict the smooth transition between the outer body 22 and the inner body 24

Referring still to FIG. 3, the inner body 24 may include an endwall 50 having a cavity 52, apertures 54, grooves 56, and protrustions 58 all configured similarly or identical to the corresponding structures of the outer body 22. As described above for the endwall 28, the endwall 50 may be angled to accommodate a particular patient anatomy or to achieve a desired vertebral alignment. A cross section of the inner body 24 perpendicular to the longitudinal axis 40 may have any of a variety of geometries and in certain embodiments may correspond to a cross section of the core member 26. Extending along the longitudinal axis 40 away from the endwall 50, a shaft 60 is configured to engage at least a portion of the chamber 44 of the outer body 22. Although the shaft portion 60 of the inner body 24 may be solid, in an alternative embodiment, the cavity 52 may extend into the shaft 60.

Opposite the endwall 50, the inner body 24 comprises an endwall 62 having a surface substantially perpendicular to longitudinal axis 40. Endwall 62 may be shaped to conform to the contours of core member 26. The shaft 60 may further comprise a laterally extending retaining tab 64 configured to slidably engage the slot 48 of the outer body 22. The tab 64 may permit slidable movement while retaining the inner body 24 and preventing the inner body 24 from disengaging the outer body 22. Where the outer body 22 comprises a plurality of slots 48, the shaft 60 may comprise a corresponding plurality of tabs 64. The tabs may, alternatively, be formed on the outer body 22 to engage slots formed on the inner body 24.

The shaft 60 may, for example, be formed as an oval cylinder or another shape that can prevent rotational movement of the inner body 24 when positioned within the chamber 44 of the outer body 22. Although depicted as a right cylinder, in an alternative embodiment, the shaft 60 may have angled walls to permit limited pivoting of the inner body 24 with respect to the longitudinal axis 40 without allowing the bodies 22 and 24 to become detached. In some embodiments, the shaft 60 may fit snugly within a portion of the chamber 44, in others, the fit may be somewhat loose, allowing play between the bodies 22 and 24. The inner body 24 may be formed in a variety of heights and widths and with a variety of endwall angulations. For example, the outer body 22 may have a height of approximately 29 mm. and an endwall angulation of 2°.

The outer body 22 and the inner body 24 may be formed from a biocompatible material suitable to withstand the application of external compressive, axial, torsional, and bending loads, as well as strong enough to provide support for the adjacent intact vertebrae. The outer and inner bodies may be formed from the same or different materials. Suitable materials may have a higher modulus than the core member 26. Suitable biocompatible materials may include metals such as titanium, titanium alloys, cobalt-chrome alloys, titanium nickel alloys, and surgical grade stainless steel. Suitable polymers may include ultra-high molecular weight polyethylene, polyaryletherketone, ployetheretherketone, polymethyl methacrylate, polyacetal, polysulfone, and polyimide. Suitable ceramic materials may include alumina, zirconia, polycrystalline diamond compact, pyrolitic carbon, and a porous tantalum material such as HEDROCEL® provided by Implex Corporation of Allendale, N.J. Suitable composite materials may include carbon-filled composites, hydroxyl-appetite-filled composites, and bioactive-glass-filled composites. A combination of any of the above materials may also be used.

The surfaces of the bodies 22 and 24 may be modified to suit particular purposes. For example, surfaces intended to contact bone may be roughened, textured, spiked, serrated, or coated with osteoconductive materials such as calcium phosphate or hydroxyl appetite. Surfaces of bodies 22 and 24 which may contact the core member 26 may be smooth, hardened, and/or lubricated for lowering friction and reducing wear and tear on the core member.

Referring still to FIG. 3, the core member 26 is configured to occupy at least a portion of the chamber 44 between the chamber base 46 and the endwall 62 of the inner body 24. The core member 26 may be formed from a homogenous and/or semi-solid material which may be inserted or injected into the cavity 40. Suitable materials may include one or more materials such as plastics, rubbers, elastomers, hydrogels, or other combinations.

Core member 26 may also be comprised of a copolymer, a blend, a composite, or a laminate of various polymers. Examples of copolymers include a copolymer of polyether urethane and silicone or a copolymer of polycarbonate urethane and silicone. An example of a blend includes a blend of the copolymers described above. Examples of a composite include polyester fabric or fibers in silicone-polyether urethane. One example of a laminate is multiple layers of silicone-polyether urethane and polyester fabric or polyethylene mesh. Another example of a laminate is multiple layers of hydrogel and polyester mesh.

The core member 26 may be comprised of an elastomer or any other flexible material capable of recovering at least some amount of its original size and shape after deformation. Suitable materials may include polyurethane, copolymers of silicone and polyurethane, silicones, polyolefin rubbers, polyvinyl alcohol hydrogels, polyacrylonitrile-based hydrogels, polyacrylic-based hydrogels, and polyurethane-based hydrogels.

Alternatively, the core member 26 may comprise a membrane or casing formed from an elastomer material and having one or more compartments filled with a hydrogel, an elastomer, a liquid, a gaseous substance, or any other appropriate material. In some embodiments the material or materials used to form the core member 26 may result in a compressible core member, but in certain other embodiments, the core member may be relatively rigid, functioning as a strut between outer body 22 and inner body 24.

As shown in FIGS. 2a and 5, the core member 26 may be formed having grooves 65a, apertures 65b (which may be vertical, horizontal or angled), or other features including indentions, isolated voids, interconnected voids which can modify the characteristics of the core member 26 such as stiffness, compliance, shock absorption, compression resistance and other characteristics that affect stress relief and enhance the device's 20 absorbtion of dynamic loads. The features may be located on or below the surface of the core member 26. In alternative embodiments, the core member 26 may have a smooth, uniform surface. As shown in FIG. 5, the cross section of the core member 26 may be generally oval. It is understood, however, that the shape of the core member 26 may be selected to conform to the shape of the chamber 44 or to the deformation requirements of the vertebral implant device 20. The geometry of the core member cross section may be round, rectangular, square, elliptical, hexagonal or any other shape useful to a particular application. In some embodiments the physical structure of the core member 26, for example a spring or coil shape, may provide the elasticity to absorb the loads applied to the device 20. The core member 26 may be a single structure or may comprise one or more discrete structures capable of being housed in the chamber 44.

As shown in FIGS. 3 and 4, the components of implant device 20 may be assembled prior to implantation. For example, the core member 26 may be inserted into the cavity 44 of the outer body. Next, tab 64 of the inner body can engage the slot 48 of the outer body 22 thereby connecting the outer body 22 to the inner body 24 and containing the core member 26 between the two bodies. The tab 64 may be permitted to move within the slot 48 thus permitting movement of the inner body 24 along the longitudinal axis 40 without allowing the bodies 22 and 24 to disengage. Both the shape of the bodies 22 and 24 and the configuration of the slot 48 and tab 64 may restrict rotational movement, ensuring that motion is limited to axial translation. It is understood that multiple tabs and slots can be used to achieve this same type of movement. With the tab 64 translating within the slot 48, the core member 26 may compress or expand as the size of the space between the cavity base 46 and the endwall 52 is varied by external forces.

Following the corpectomy removing vertebra 12a, for example, the space may be evaluated to determine the correct size and endplate orientation. If modular components are available, a care giver may select the components having the size, shape, and angle best suited to fit the space and to accommodate the requirements of a particular patient. Further, the core elasticity may be selected to correspond to patient weight or desired spinal loads to best suit the prosthesis to the patient. In some embodiments the components may be assembled in the surgical arena, and in other embodiments, the components may be pre-assembled in a factory or in another facility which pre-assembles and distributes assembled components to care providers.

The pre-assembled implant device 20 may be inserted into the vertebral column 10 between the remaining vertebrae 12b and 12c. Before insertion, each of the cavities 32 and 52 may be packed with bone growth promoting material to facilitate bone growth and stability of the implanted device 20. The device 20 may be oriented such that the outer body 22 is in the rostral position, but in an alternative embodiment, the inner body 24 may be in the rostral position.

Referring now to FIG. 6, in one embodiment, the device 20 may be compressed during installation to permit insertion of the device 20 without damaging the adjacent vertebrae. The maximum compression of the device 20 may be limited by several features of the device 20 including the elasticity of the core member 26, the length and position of the slot 48, and the size of the chamber 44. An insertion instrument 66 may be used to facilitate installation of the implant device 20. The insertion instrument 66 may, for example, engage the grooves 38 and 56 of the bodies 22 and 24 with prongs 68 which can apply a compressive force for compacting the device 20. One embodiment of the insertion instrument 66 is disclosed in U.S. patent application Ser. No. 10/441,689 which is incorporated by reference herein. When the device 20 is sufficiently compacted to permit installation in the space between the vertebrae 12b and 12c, the insertion instrument 66 can be used to move the device 20 into place. After the device 20 is positioned within the spinal column 10, the prongs 68 of the insertion instrument 66 may be extracted.

Once located in the space vacated by vertebra 12a, the device 20 may be allowed to expand to occupy the space. In some embodiments, however, the core member can remain under at least some amount of compression after the device 20 is located in the vertebral column and allowed to expand. After expansion, the endwall 30 can engage the endplate of vertebra 12b, and the endwall 50 can engage the endplate of the vertebra 12c. Specifically, the protrusions 36 may press against the adjacent vertebral endplates, mechanically holding the device 20 in place. Additionally or alternatively, the bodies 22 and 24 may be fused to the adjacent vertebrae through bone ingrowth into the upper and lower cavities. Alternatively, the bodies 22 and 24 may be cemented or chemically bonded with other methods known in the art. The compressive forces exerted by the adjacent vertebrae 12b and 12c on the device 20 may further operate to ensure a consistent, intimate contact between the device and the vertebrae. If necessary, after installation additional bone growth promoting material may be inserted into the cavities 32 and 52 through the apertures 34 and 54.

In certain embodiments, the device 20 may be inserted into the vertebral column without first compressing the device. In such an embodiment, following the removal of the vertebra 12a, the remaining vertebrae 12b and 12c may be distracted to maintain or increase the separating space. The device then be installed without compression.

After installation, the elasticity of the core member 26 and the limited movement of the translatable inner body 24 can permit movement within the device 20 to dissipate dynamic loads, thereby reducing the risk of subsidence and other forms of damage to the remaining vertebrae and discs in the vertebral column 10. The shape of the cavity 44, the configuration of the core member 26, and the amount of play between the outer body 22 and the inner body 24 can allow the vertebral implant device 20 to accommodate aligment imperfections. Over time, the outer body 22 and inner body 24 may settle into their adjacent vertebral endplates, increasing the spacing between the vertebral endplates. Embodiments in which the core member 26 is held in compression after installation accommodate this settlement by allowing the core member 26 to continue exerting pressure on the bodies 22 and 24 to maintain good anchorage and to promote fusion.

Referring now to FIG. 7, in another embodiment of the present invention, the implant device 20 includes the outer body 22, the core member 26, a second outer body 70, a second core member 72 and a center shaft 74. The second outer body 70 and the second core member 72 may be similar or identical to the outer body 22 and the core member 26, respectively, and therefore, these components will not be described in detail except to define a chamber 76 and a slot 78 in the second outer body 70 which correspond to the chamber 44 and the slot 48, respectively. The center shaft 74 extends between the core member 26 and the core member 72. The center shaft 74 comprises an end portion 80 configured to engage chamber 44 and an end portion 82 configured to engage cavity 76. End portion 80 may include a laterally extending tab 84 configured to slidably engage the slot 48 of the outer body 22. The end portion 82 may also include a laterally extending tab 86 configured to slidably engage the slot 78 of the second outer body 70. Where the outer bodies 22 and 70 comprise a plurality of slots, the center shaft 74 may comprise a corresponding plurality of tabs.

Referring now to FIG. 8, The device 20 may be preassembled such that the core member 26 is positioned within the chamber 44, and the core member 72 is positioned within the chamber 76. The tab 84 of the center shaft 74 may engage slot 48 and the tab 86 may engage slot 78, thereby containing the core members 26 and 72 within the respective chambers. The device 20 may be installed in a manner similar to that disclosed above. After installation, the translatable center shaft 74 and the pair of core members 26 and 72 allow the device 20 to dampen dynamic loads applied to the vertebral column.

It is understood that particular features of the center shaft 74 and the outer bodies 22 and 70 may be interchanged. For example, the center shaft 74 may incorporate chambers for housing the core members, in which case, the outer bodies 22 and 70 may comprise shaft portions configured to engage the cavities of the center shaft. The center shaft 74 may further include slots configured to engage tabs located on the outer bodies 22 and 70.

To accommodate a variety of surgical applications, the device 20 may include multiple center shafts and more than two core members. It is understood that the various features of the center shafts and outer bodies may be interchanged to achieve the coupling of multiple components.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A vertebral implant device for interposition between two vertebral bodies, the device comprising:
    an outer body including a chamber and a first vertebral interface endwall textured for engagement with one of the two vertebral bodies;
    an inner body including a second vertebral interface endwall textured for engagement with the other of the two vertebral bodies, wherein the outer body includes at least one slot and the inner body includes at least one tab, and wherein the tab movably engages the slot; and
    a core member positioned entirely within the chamber,
    wherein the outer body is movably engaged with the inner body and wherein responsive to a load applied to the device, the outer and inner body at least partially compress the core member and,
    wherein the outer body and inner body each comprise a cavity for containing bone growth promoting material.

2. The vertebral implant device of claim 1 wherein the inner body comprises a shaft extending at least partially into the chamber.

3. The vertebral implant device of claim 2 wherein responsive to the load applied to the device, the shaft slidably advances into the chamber causing the at least partial compression of the core member.

4. The vertebral implant device of claim 1 further comprising a longitudinal axis, wherein the slot extends longitudinally along the outer body and the tab translates within the slot for movably engaging the outer and inner bodies.

5. The vertebral implant device of claim 1 wherein the tab prevents the inner body from disengaging the outer body.

6. The vertebral implant device of claim 1 wherein the outer body comprises one or more apertures in communication with the cavity.

7. The vertebral implant device of claim 1 wherein the outer body includes a longitudinal axis and an end portion extending at a non-perpendicular angle with respect to the longitudinal axis.

8. The vertebral implant device of claim 1 wherein the inner body includes a longitudinal axis and an end portion extending at a non-perpendicular angle with respect to the longitudinal axis.

9. The vertebral implant device of claim 1 wherein the device includes a substantially oval cylindrical cross-section.

10. The vertebral implant device of claim 1 wherein the core member comprises one or more compartments.

11. The vertebral implant device of claim 1 wherein the core member comprises an elastomer.

12. The vertebral implant device of claim 11 wherein the elastomer comprises polyurethane.

13. The vertebral implant device of claim 11 wherein the elastomer comprises silicone.

14. The vertebral implant device of claim 11 wherein the elastomer comprises a copolymer of polyurethane and silicone.

15. The vertebral implant device of claim 11 wherein the elastomer comprises polyolefin rubber.

16. The vertebral implant device of claim 1 wherein the core member comprises a hydrogel.

17. The vertebral implant device of claim 16 wherein the hydrogel comprises a polyvinyl alcohol hydrogel.

18. The vertebral implant device of claim 16 wherein the hydrogel comprises a polyacrylonitrile-based hydrogel.

19. The vertebral implant device of claim 16 wherein the hydrogel comprises a polyacrylic-based hydrogel.

20. The vertebral implant device of claim 16 wherein the hydrogel comprises a polyurethane-based hydrogel.

21. The vertebral implant device of claim 1 wherein the core member comprises one or more polymers.

22. The vertebral implant device of claim 1 wherein the core member comprises one or more surface features for altering the response of the core member to the at least partial compression.

23. The vertebral implant device of claim 1 wherein the core member comprises one or more subsurface features for altering the response of the core member to the at least partial compression.

* * * * *